US005707807A

United States Patent [19]

Kato

[11] Patent Number: 5,707,807
[45] Date of Patent: Jan. 13, 1998

[54] MOLECULAR INDEXING FOR EXPRESSED GENE ANALYSIS

[75] Inventor: Kikuya Kato, Osaka, Japan

[73] Assignee: Research Development Corporation of Japan, Japan

[21] Appl. No.: 621,914

[22] Filed: Mar. 26, 1996

[30] Foreign Application Priority Data

| Mar. 28, 1995 | [JP] | Japan | 7-069695 |
| Jul. 20, 1995 | [JP] | Japan | 7-184006 |
| Sep. 12, 1995 | [JP] | Japan | 7-234122 |

[51] Int. Cl.⁶ .............. C12Q 1/68; C12Q 1/70; C12P 19/34; C07N 21/04
[52] U.S. Cl. .............. 435/6; 435/91.1; 435/91.2; 435/91.5; 435/5; 536/24.3; 536/24.33
[58] Field of Search .............. 435/6, 5, 91.1, 435/91.5, 91.2; 536/24.3, 24.33

[56] References Cited

U.S. PATENT DOCUMENTS 5,508,169  4/1996  Deugau .............. 435/6

FOREIGN PATENT DOCUMENTS

| WO 93/06239 | 4/1993 | WIPO. |
| WO 93/18176 | 9/1993 | WIPO. |
| WO 94/01582 | 1/1994 | WIPO. |
| WO 94/11383 | 5/1994 | WIPO. |
| WO 95/13369 | 5/1995 | WIPO. |

OTHER PUBLICATIONS

K. Kato, 1995, "Description of the entire mRNA population by a 3' end cDNA fragment generated by class IIS restriction enzymes", *Nuc. Acids Res.* 23:3685–3690.

McClelland et al., 1995, "RNA fingerprinting and differential display using arbitrarily primed PCR", *TIG* 11:242–246.

Schena et al., 1995, "Quantitative monitoring of gene expression patterns with a complementary DNA microarray", *Science* 270:467–470.

D.R. Smith, 1992, "Ligation-mediated PCR of restriction fragments from large DNA molecules", *PCR Methods and Applications* 2:21–27.

Velculescu et al., 1995, "Serial analysis of gene expression", *Science* 270:484–487.

Wang et al. PNAS 88: 11505–11509, 1991.

Liang et al. Science 257:967–971, 1992.

Hakvoort et al. Nucleic Acids Research 22:879–79, 1994.

Brenner and Livak, PNAS 86:8902–6, 1992.

Unrau et al. Gene 145: 163–169, 1994.

*Primary Examiner*—W. Gary Jones
*Assistant Examiner*—Dianne Rees
*Attorney, Agent, or Firm*—Pennie & Edmonds LLP

[57] ABSTRACT

This invention relates to a method for classifying (indexing) cDNA which has been reverse-transcribed from tissue- or cell-derived RNA, or DNA in a short period without duplication by using class-IIS restriction enzymes or a combination of a class-IIS and a class-II restriction enzymes. According to this invention, it is possible to analyse and diagnose variations such as tumors easily, correctly and promptly by comparing the analyzed pattern of genes expressed in a cell or tissue sample with the analyzed pattern of normal genes. This method is also applicable to the search and isolation of genes of physiologically active substances that are potential pharmaceuticals or causative genes of hereditary diseases, as well as the isolation of those genes that are useful for improving agricultural products.

15 Claims, 5 Drawing Sheets

When the base adjacent to polyA on the 5' side is T:

$$-------- TA_{16}GGATCC$$
$$-------- AT_{16}CCATGG$$

When the base adjacent to polyA on the 5' side is G:

$$-------- GA_{16}CAGCTG$$
$$-------- CT_{16}GTCGAC$$

When the base adjacent to polyA on the 5' side is C:

$$-------- CA_{16}CTCGAG$$
$$-------- GT_{16}GAGCTC$$

FIG. 2

MOLECULAR INDEXING FOR EXPRESSED GENE ANALYSIS

FIELD OF THE INVENTION

This invention relates to a method for molecular indexing which is applicable to the analysis and diagnosis of diseases such as cancers, the search and isolation of genes of physiologically active substances that are potential pharmaceuticals or causative genes of hereditary diseases, as well as the isolation of those genes that are useful for improving agricultural products.

BACKGROUND OF THE INVENTION

For examining differences in gene expression between two tissues, there has been described a method wherein a portion (about 50-200 genes) of the expressed gene population is amplified by PCR (the polymerase chain reaction method) using any short primers and then separated by polyacrylamide gel electrophoresis [P. Liang and A. B. Pardee, Differential display of eukaryotic messenger RNA by means of the polymerase chain reaction, Science 257:967-971 (1992)]. However, in such differential display by means of PCR, only a portion of the whole gene population is amplified in principle and yet a plurality of bands are generated from the same gene. Furthermore, such display involves a large quantity of artifacts and thus is technically incomplete. Therefore, such display only shows differences in gene expression between two tissues which are not remote from each other or differences in gene expression in cells. Such differential display has a problem that it cannot record the expression of individual genes.

It is also possible to analyze variations in tissues or cells by determining the level of a particular gene in such tissues or cells through measuring the amount of its mRNA by Northern blot hybridization method. However, this method is not applicable when the target gene is not cloned or the base sequence thereof is unknown. In addition, this method is not suitable for the analysis of a large number of genes. For example, since genes being expressed in a certain cell are considered about 10,000 species, it will take for about two years even if Northern blot hybridization is performed for 100 genes per week. Thus, this method is not practically useful.

On the other hand, those restriction enzymes which belong to class IIS (hereinafter, referred to as "class-IIS restriction enzymes") are restriction enzymes having an ability to cut at a precise distance outside their recognition sites. Those fragments cut by a class-IIS restriction enzyme are characterized to have non-identical, cohesive ends consisting of several nucleotides. There have been known more than 30 class-IIS restriction enzymes including Fok I, Bsm FI, Bsm AI, Bbv I, Sfa NI and Hga I. It is estimated that genes which have at least one cleavage site of Fok I, Bsm FI or Bsm AI will be 97% of total genes. Brenner et al. has introduced a method of preparing a more detailed genome map using a class-IIS restriction enzyme which generates 4-nt (nucleotide) sequences in place of conventional restriction enzymes [S. Brenner and K. J. Livak, DNA fingerprinting by sampled sequencing, Proc. Natl. Acad. Sci. U.S.A., 86:8902-6 (1989)]. There is also disclosed a method wherein a part of restriction enzyme fragments derived from a phage or cosmid is amplified by using those adaptors which are complementary to all possible 4-nt cohesive ends generated by class-IIS restriction enzymes [D. R. Smith, ligation-mediated PCR or restriction fragments from large DNA molecules, PCR Methods Appl. 2:21-27 (1992); Unrau, P. and Deugau, K. V., Gene, 145, 163-169 (1994)]. However, though all of these methods employ class-IIS restriction enzymes and use the 4-nt overhangs generated by them as means for structural analysis of genomes, unlike the present invention, they do not aim at recording the expression of genes in a specific tissue or cell.

In the Human Genome Project, there is vigorously argued an approach to take a tissue-derived cDNA fragment as a sample and to determine a partial sequence thereof as well as its location in a chromosome. In conventional methods, cDNA fragments are randomly taken from cDNA library. Accordingly, it is impossible to avoid a repeated sampling of the same fragment and there is a tendency that highly expressed fragments are selectively taken.

It is an object of the present invention to provide a method which can analyze the state of expression of genes or deletion due to some abnormalities in a tissue or a cell in a short period and yet easily for a large quantity of genes.

It is a further object of the present invention to provide a method which is applicable to a rapid isolation of the coding region of a protein as well as an amplification of restriction fragments of cloned DNA or genomic DNA.

SUMMARY OF THE INVENTION

The present inventor has made extensive and intensive researches toward the solution of the above assignment and, as a result, found that, by using class-IIS restriction enzymes or a combination of a class-IIS enzyme and a class-II restriction enzyme, it is possible to classify (index) cDNA or DNA into groups in a short period and without duplication. Thus, the present invention has been achieved.

The present invention relates to a method for molecular indexing comprising the following steps (hereinafter referred to as "Method I"):

(1) digesting cDNA which has been reverse-transcribed from tissue- or cell-derived RNA with a first restriction enzyme of class-IIS, (2) ligating each of the resultant cDNA fragments to one from a pool of 64 biotinylated adaptors cohesive to all possible overhangs, (3) digesting the resultant cDNA fragments further with a second and a third restriction enzymes of class-IIS which are different from the first class-IIS restriction enzyme used in (1) above to thereby obtain a first cDNA sample, (4) obtaining a second cDNA sample by repeating the above steps (1) to (3) wherein the second class-IIS restriction enzyme is used for the initial digestion and the first and the third class-IIS restriction enzymes are used for the subsequent digestion, (5) obtaining a third cDNA sample by repeating the above steps (1) to (3) wherein the third class-IIS restriction enzyme is used for the initial digestion and the first and the second class-IIS restriction enzymes are used for the subsequent digestion, (6) recovering each of the resultant ligation samples by using streptavidin-coated paramagnetic beads and then removing from the samples the oligonucleotide complementary to an adaptor-primer to be used in (7), (7) amplifying each of the resultant cDNA samples by PCR using an adaptor-primer and one of anchored oligo-dT primers, (8) separating the amplified products by denaturing polyacrylamide gel electrophoresis and recording the sizes of the fragments obtained.

The present invention also relates to a method for molecular indexing comprising the following steps (hereinafter referred to as "Method II"):

(1) digesting cDNA which has been reverse-transcribed from tissue- or cell-derived RNA, or DNA with a restriction enzyme of class-II, (2) ligating each of the resultant cDNA or DNA fragments to an adaptor cohesive to ends generated by the class-II restriction enzyme, (3) digesting the resultant cDNA or DNA fragments further with a restriction enzyme of class-IIS, (4) ligating each of the resultant cDNA or DNA fragments to one from a pool of 64 biotinylated adaptors cohesive to all possible overhangs, (5) recovering the resultant ligated sample by using streptavidin-coated paramagnetic beads and then removing from said sample the oligonucleotides complementary to adaptor-primers to be used in (6), (6) amplifying the resultant cDNA or DNA sample by PCR using adaptor-primers, (7) separating the amplified products by denaturing polyacrylamide gel electrophoresis and recording the sizes of the fragments obtained.

BRIEF DESCRIPTION OF THE DRAWINGS

FIG. 2 shows structures of cDNA which has been synthesized by reverse-transcribing RNA using a mixture of 3 oligonucleotides as primers.

EFFECT OF THE INVENTION

Figure 1:
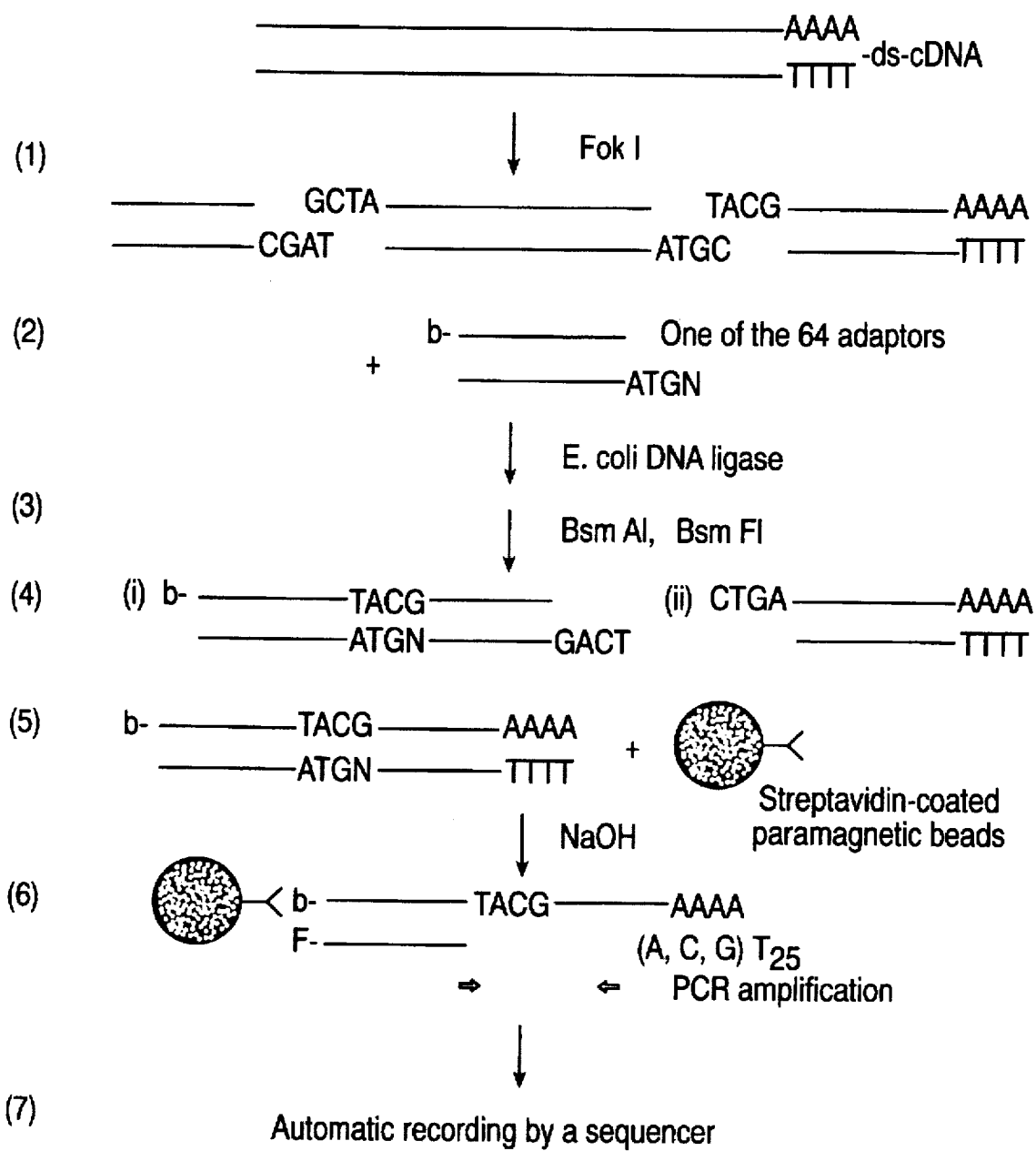
FIG. 1 shows a schematic illustration for the principle of Method I. N is a mixture of A, C, G and T.

According to Method I, it is possible to examine the state of expression of those genes having cleavage sites of class-IIS restriction enzymes (97% of total genes are estimated to have such sites when Fok I, Bsm AI and Bsm FI are used) in a tissue with one to two week experiment per one human subject, since a small number of DNA sub-groups will do for this analysis. Furthermore, according to Method I, since the number of fragments amplified from one gene is only one in principle, genes can be classified (indexed) into sub-groups without redundancy. Therefore, by comparing the analyzed pattern between normal and abnormal tissues by using Method I, it is possible to diagnose variations such as tumors easily, correctly and promptly. In addition, Method I is also applicable to the search and isolation of genes of physiologically active substances that are potential pharmaceuticals or the causative genes of hereditary diseases, as well as the isolation of those genes that are useful for improving agricultural products.

On the other hand, according to Method II, the target of analysis is not limited to RNA (or cDNA reverse-transcribed therefrom), since oligo-dT primers for poly A are not used as primers. According to Method II, it is also possible to amplify restriction fragments of cosmid DNA or genomic DNA. Therefore, Method II is applicable to the mapping of these DNAs.

In addition, regions amplified by PCR is not restricted to non-coding regions and thus it is not necessary to obtain clones of upstream regions in order to know the primary structure of a protein.

DETAILED DESCRIPTION OF THE INVENTION

[I] Hereinbelow, the steps, action and effects of Method I will be described with reference to FIG. 1.

(1) First, the total RNA of a cell or a tissue is converted to cDNA with a reverse-transcriptase and the resultant cDNA is digested with a first class-IIS restriction enzyme.

(2) One from a pool of 64 biotinylated adaptors described below is ligated to the resultant cDNA fragments with $E.$ $coli$ DNA ligase. Each adaptor has a 4-nt 5' end overhang wherein the outermost base is a mixture of A, C, G and T and the inner three bases are one of all possible sequences. (These adaptors must not be phosphorylated at their 5' ends which form protruding cohesive ends.) At this point, the restriction fragments are classified into 64 sub-groups.

(3) Subsequently, the cDNA fragments are further digested with a second and a third class-IIS restriction enzymes which are different from the first class-IIS restriction enzyme used in (1) above to thereby obtain a first cDNA sample.

A second cDNA sample is obtained by repeating the above steps (1) to (3) wherein the second class-IIS restriction enzyme is used for the initial digestion and the first and the third class-IIS restriction enzymes are used for the subsequent digestion, and also a third cDNA sample is obtained by repeating the above steps (1) to (3) wherein the third class-IIS restriction enzyme is used for the initial digestion and the first and the second class-IIS restriction enzymes are used for the subsequent digestion.

(4) As a result of digestion with the 3 class-IIS restriction enzymes described above, there are produced fragments which have lost poly A [see FIG. 1, (2)] and fragments which still have poly A [see FIG. 1, (ii)]. Of these fragments, the former ones which have lost poly A will no longer be amplified in the subsequent amplification step and only the latter ones with poly A will be amplified. Accordingly, the latter fragments are further classified into 64×3=192 sub-groups at this point depending on the cleavage site nearest the poly A side (i.e., depending on the cleavage site of which of the three restriction enzymes used).

(5) Subsequently, the ligation sample is recovered with streptavidin-coated paramagnetic beads and the cDNA fragments are treated with a dilute alkaline solution. By these operations, the oligonucleotide complementary to an adaptor-primer to be used in (6) is removed (the oligonucleotide will become an inhibitor against PCR reaction).

(6) The resultant cDNA sample is amplified by PCR by using a combination of an adaptor-primer and one of d(T)$_{25}$A(SEQ ID NO:1), d(T)$_{25}$C (SEQ ID NO:2) and d(T)$_{25}$G (SEQ ID NO:3) which are anchored oligo-dT primers. Depending on the base (T, C or G) adjacent to the poly(A) tail, fragments amplified by the above three oligo-dT primers are determined. At this point, the cDNA fragments are further classified into 192×3=576 groups.

(7) The amplified products are separated by denaturing polyacrylamide gel electrophoresis and the sizes of the fragments obtained are automatically recorded by a sequencer.

The above-described procedures are repeated with 64 adaptors, 3 class-IIS restriction enzymes and 3 anchored oligo-dT primers. Therefore, an RNA population is classified into 576 groups. With respect to class-IIS restriction enzymes, it is estimated that 97% of genes have at least one cleavage site of Fok I, Bsm AI or Bsm FI.

Accordingly, by using these 3 restriction enzymes in the method of the invention, it is theoretically possible to recover and present without redundancy almost all of one total RNA population.

In addition, the above method (Method I) of the invention may be similarly carried out in a modified method which is different from the above only in the following points. In step (2) above, one from a pool of 256 biotinylated adaptors is used. Each adaptor of the pool has a four-nucleotide 5' end overhang wherein the sequence is one of all possible sequences. The second digestion with class-IIS restriction enzymes described in (3) above is not carried out.

In this modified method, an RNA population is classified into 768 groups since 256 adaptors and 3 anchored oligo-dT primers are used.

Further, in Method I, a mixture of the following oligonucleotides may be used as primers when converting the total RNA from a cell or tissue into cDNA with a reverse transcriptase:

5' OH—GGATCCT$_{16}$A-3'  (SEQ ID NO:4)

5' OH—CAGCTGT$_{16}$C-3'  (SEQ ID NO:5)

5' OH—CTCGAGT$_{16}$G-3'  SEQ ID NO:6)

When such primers are used, there can be obtained cDNA molecules which have T, G or C adjacent to poly (A) on the 5' side and a 6-base sequence added to the outside (3' side) of poly A) (see FIG. 2).

In this case, amplification is carried out by using any one of 5'OH-GGATCCT$_{16}$A-3' [instead of the above anchored oligo-dT primer d(T)$_{25}$A],5'OH-CAGCTGT$_{16}$C-3' [instead of the above d(T)$_{25}$C] and 5'OH-CTCGAGT$_{16}$G-3' [instead of the above d(T)$_{25}$G]. According to these procedures, analysis can be more correct because, in addition to the specificity to cDNA of only one base of the 3' end of primers, specificity to cDNA by the 6-base sequence of the 5' end of primers is utilized.

The target RNA for Method I of the invention is isolated and purified from, for example, body tissues such as hematopoietic tissues including bone marrow, peripheral blood, lymphocytes, etc. or cells in a body fluid by conventional methods such as the guanidine thiocyanate method and the phenol-chloroform extraction method and then incubated with a reverse transcriptase and deoxyribonucleotide triphosphates for reverse-transcription into cDNA.

With respect to the class-IIS restriction enzymes used in Method I of the invention, there is no particular limitation as long as the restriction enzyme forms a 5'-protruding cohesive end consisting of 4 bases. Specific examples include commercially available Fok I (Takara Shuzo) and Bsm AI and Bsm FI (both manufactured by NEB). These three restriction enzymes may be used in combination for the initial digestion (with one enzyme) and the subsequent digestion (with two enzymes). In the modified method, one of these three enzymes may be used.

In Method I of the invention, the biotinylated adaptor means the adaptor consisting of i) an oligonucleotide of 24–27 nucleotides which forms a 4-nt 5' protruding cohesive end wherein the outermost base is a mixture of A, C, G and T, and inter three bases are one of all possible sequences, and ii) an oligonucleotide which is complementary to the oligonucleotide i), shorter by 4 bases and biotinylated at the 5' end. Thus, there are 64 kinds of the biotinylated adaptors.

In the modified method, the biotinylated adaptor means the adaptor consisting of i) an oligonucleotide of 24–27 nucleotides which forms a 4-nt 5' protruding cohesive end wherein the sequence is one of all possible sequences, and ii) an oligonucleotide which is complementary to the oligonucleotide i), shorter by 4 bases and biotinylated at the 5' end. Thus, there are 256 kinds of the biotinylated adaptors.

In order to allow E. coli DNA ligase to recognize the 3 bases of a cDNA fragment adjacent to the binding site, phosphorylation of the 5' ends of the above adaptors which form cohesive ends is not carried out.

In Method I of the invention, one of the two primers used for PCR is an oligonucleotide having a common sequence with the oligonucleotide constituting the adaptor described above which is subjected to ligation to cDNA at 3' end (=adaptor-primer). As a marker which labels this adaptor-primer, those which are used in conventional analysis may be used. Specific examples include fluorescent dyes, radioactive materials and enzymes.

In Method I of the invention, another primer used for PCR is one of three oligo-dT primers, of which 3' end base is A, C or G. These primers may be synthesized by a commercial nucleic acid synthesizer.

[II] Hereinbelow, the steps, action and effects of Method II will be described with reference to FIG. 3.

Figure 3:
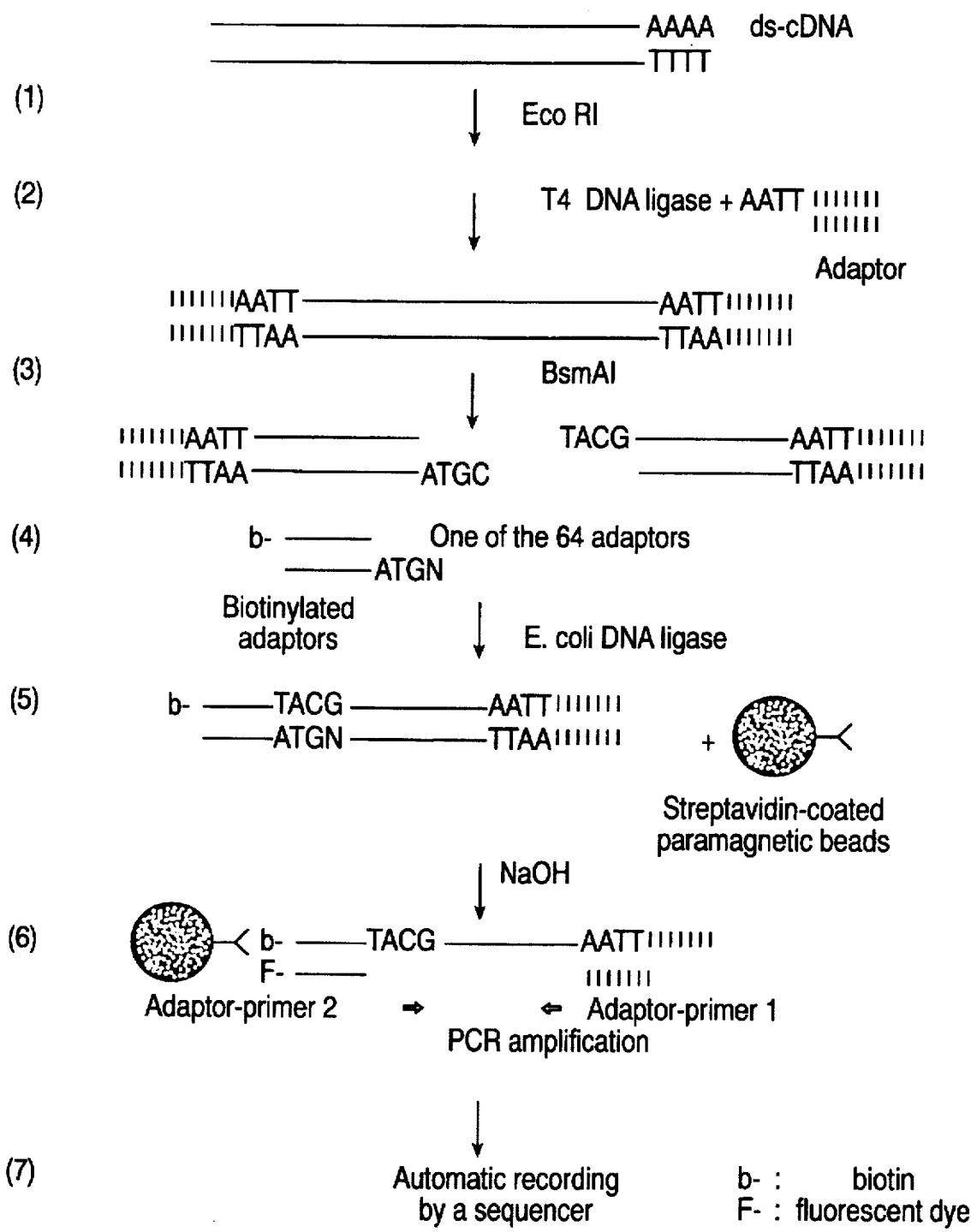
FIG. 3 shows a schematic illustration for the principle of Method II. N is a mixture of A, C, G and T.

(1) First, DNA or cDNA of a cell or tissue is digested with a class-II restriction enzyme (EcoRI is used in FIG. 3).

(2) An adaptor which is cohesive to ends generated by the class-II enzyme is ligated to each of the DNA or cDNA fragments with T4 DNA ligase (the adaptor must be phosphorylated at the 5' end which form cohesive ends).

(3) The resultant DNA or cDNA sample is further digested with a class-IIS restriction enzyme (Bsm AI is used in FIG. 3).

(4) One from a pool of 64 biotinylated adaptors described below is ligated to each of the resultant cDNA or DNA fragments with E. coli DNA ligase. Each adaptor has a 4-nt 5' end overhang wherein the outermost base is a mixture of A, C, G and T, and the inner three bases are one of all possible sequences. (These adaptors must not be phosphorylated at their 5' ends which form cohesive ends.) At this point, the restriction fragments are classified into 64 groups.

(5) Subsequently, the ligation sample is recovered with streptavidin-coated paramagnetic beads and the DNA or cDNA fragments are treated with a dilute alkaline solution. By these operations, those oligonucleotides complementary to adaptor-primers which will become inhibitors against PCR reaction are removed.

(6) Amplification by PCR is carried out using two adaptor-primers. The one derived from the adaptor for ends generated by the class-II enzyme is referred to as "adaptor-primer 1" and the other derived from the biotinylated adaptors is referred to as "adaptor-primer 2". Details will be described afterwards.

(7) The amplified products are separated by denaturing polyacrylamide gel electrophoresis and the sizes of the fragments obtained are automatically recorded by a sequencer.

By using a class-II restriction enzyme, a class-IIS restriction enzyme and 64 biotinylated adaptors in the operations described above, the DNA or cDNA fragments generated by the class-II and class-IIS restriction enzymes used can be separated and displayed.

When cDNA which has been reverse-transcribed from RNA is used as a target of analysis of Method II, a cDNA sample is prepared as follows. RNA is isolated and purified from, for example, body tissues such as hematopoietic tissues including bone marrow, peripheral blood, lymphocytes, etc. or cells in a body fluid by conventional methods such as the guanidine thiocyanate method and the phenol-chloroform extraction method and then incubated with a reverse transcriptase and deoxyribonucleotide triphosphates for reverse-transcription into cDNA.

It is also possible to use DNA as a target of analysis of Method II. In this case, a DNA sample is prepared as follows. DNA isolated from, for example, body tissues such as hematopoietic tissues including bone marrow, peripheral blood, lymphocytes, etc. or a cell suspension in a body fluid is crushed with polytron or the like and incubated with proteinase K to thereby degrade proteins. Then, the reaction solution is subjected to phenol extraction and 2 volumes of ethanol is added to the aqueous layer for precipitation. The precipitate is treated with ribonuclease (RNase) not containing deoxyribonuclease (DNase) to thereby remove RNA.

With respect to the class-II restriction enzyme used in Method II of the invention, there is no particular limitation as long as the enzyme recognizes a specific base sequence, cut the site specifically and generate cohesive ends. Specific examples include EcoRI, BamHI, HindIII, BclII, BglII, SalI, XhoI, AccI, AvaI, Sau3A, TaqI, NotI (which form 5'-protruding cohesive ends), and PstI, SacI, KpnI, HaeII (which form 3'-protruding ends).

In particular, for the analysis of genomic DNA, restriction enzymes which recognize a 8-base sequence (e.g., NotI) are preferably used.

With respect to the class-IIS restriction enzyme used in Method II of the invention, there is no particular limitation as long as the enzyme generates 4-base 5'-protruding cohesive ends. Specific examples include commercially available Fok I (Takara Shuzo) and Bsm AI, Bsm FI, SfaNI and BbvI (all manufactured by NEB).

It is also possible to use 2 or 3 class-IIS restriction enzymes in combination to increase the number of groups as described in Method I.

In Method II of the invention, the adaptor consists of i) an oligonucleotide of 20–30 nucleotides forming a 5'- (or 3'-) overhang which is cohesive to ends of restriction fragments, and ii) an oligonucleotide which is complementary to the above oligonucleotide i) and shorter by the number of bases forming the overhang.

The adaptor must be phosphorylated at its 5' end (which form a cohesive end) so that an adaptor oligonucleotide is bound to the DNA strand which is recovered with streptavidin-coated beads.

In Method II of the invention, the biotinylated adaptor means the adaptor consisting of i) an oligonucleotide of 24–27 nucleotides which forms a 4-nt 5' protruding cohesive end wherein the outermost base is a mixture of A, C, G and T and inner three bases are one of all possible sequences, and ii) an oligonucleotide which is complementary to the oligonucleotide i), shorter by 4 bases and biotinylated at the 5' end. Thus, there are 64 kinds of the biotinylated adaptors.

In order to allow E. coli DNA ligase to recognize the 3 bases of a cDNA fragment adjacent to the binding site, phosphorylation of the 5' end of the above biotinylated adaptor which form a cohesive end is not carried out.

In Method II, one of the primers used in PCR is an oligonucleotide having a common sequence with the oligonucleotide constituting the adaptor described above which is subjected to ligation to cDNA or DNA fragments at its 3' end (adaptor-primer 1)

In Method II of the invention, another primer used for PCR is an oligonucleotide having a common sequence with the oligonucleotide constituting the biotinylated adaptor described above which is subjected to ligation to cDNA or DNA fragments at its 3' end (adaptor-primer 2). As a marker which labels this adaptor-primer, those which are used in conventional analysis may be used. Specific examples include fluorescent dyes, radioactive materials and enzymes.

These primers may be synthesized by using a commercial nucleic acid synthesizer.

Potential target diseases which may be analyzed or diagnosed by Method I or Method II of the invention include malignant tumors such as brain tumor, stomach cancer, large intestine cancer, breast cancer, uterus cancer, skin cancer, prostate cancer and malignant melanoma; virus infections such as herpes group infections, chronic hepatitis, cytomegalovirus infection and acquired immunodeficiency syndrome; and multifactorial hereditary diseases such as diabetes and hypertension.

PREFERRED EMBODIMENTS OF THE INVENTION

The present invention will be described in more detail below with reference to the following Reference Example and Examples, which are provided for the purpose of explanation and should not be construed as limiting the scope of the invention.

Reference Example

Preparation of cDNA (1) Purification of RNA by Ultracentrifugation

Mouse livers lyophilized in dry ice or liquid nitrogen were crushed with a homogenizer. To the crushed material, 5 volumes of a GuCNS solution was added at room temperature and agitated with a vortex mixer.

To a 10 ml polyallomer tube, 3.5 ml of 5.7M CsCl/0.1M EDTA solution was added and 6 ml of the resultant sample was layered over and then centrifuged overnight at 15° C. at 32000 rpm using Beckman L70 centrifuge.

(2) Recovery of the RNA after Ultracentrifugation

The tube was removed from the rotor and all of the supernatant was discarded. The tube wall was wiped and dried. Thereafter, the precipitate was dissolved in 300 µl of TE buffer.

(3) Ethanol Precipitation

To the aqueous layer, 1/10 volume of 3M potassium acetate (pH 5.0) was added, mixed gently and placed in ice. Then, 2.5 volumes of ice-cooled ethanol was added to the above mixture and mixed gently. The resultant mixture was left at −80° C. for several hours and centrifuged at 4° C. for 5 minutes to precipitate RNA. The ethanol was discarded. The RNA precipitate was washed with ice-cooled 70% ethanol and re-centrifuged to precipitate RNA. After the ethanol was discarded, the RNA precipitate was dried.

The above precipitate was dissolved in about 100 µl of sterile distilled water per 1 g of the tissue cells to obtain an RNA solution (RNA concentration=approx. 5 µg/µl).

(4) Preparation of cDNA Template (4-1) Preparation of Single-Stranded cDNA Molecules First, the resultant RNA and oligo-dT primers only were heated at 70° C. for 2–3 minutes. Then, other reagents were added thereto and kept at 37° C. for 1 hour to synthesize cDNA molecules.

| * Composition of the reaction solution | |
|---|---|
| 5x Reverse transcriptase buffer (Gibco-BRL) | 4 µl |
| 2mM dNTP (Pharmacia) | 4 µl |
| 0.1M DTT | 2 µl |
| 10 pmol/µl 5'-amino (dT)$_{18}$(SEQ ID NO:16) | 1 µl |
| Total RNA (3 µg) and distilled water | 7.5 µl |
| RNase inhibitor *[1] (40 u/ µl) (Toyobo) | 0.5 µl |
| 200 u/ µl M-MLV Reverse transcriptase*[2] (Gibco-BRL) | 1 µl |

*[1] derived from human placentas
*[2] Molony Murine Leukemia Virus (4-2) Synthesis of Double-Stranded cDNA Molecules The reaction solution described below was added to the single-stranded cDNA reaction solution and kept at 16° C. for 2 hours to thereby prepare double-stranded cDNA molecules. After the completion of the reaction, 3 µl of 0.2M EDTA (pH 7.5) and 2 µl of 5M NaCl were added thereto. Then, phenol extraction and ethanol precipitation were conducted and the precipitate was dissolved in 240 µl of distilled water.

| * Composition of the reaction solution | |
|---|---|
| 10 mM MgCl$_2$ | 70 µl |
| 1M Tris-Cl (pH 7.5) | 10 µl |
| 1M (NH$_4$)$_2$ SO$_4$ | 1.5 µl |
| RNase H (Toyobo) (1 u/ µl) | 1.5 µl |
| E. coli DNA polymerase I (Toyobo) (10 u/µl) | 4.5 µl |

EXAMPLE 1

Analysis by the DNA Molecular Indexing Method (1) Digestion with a Class-IIS Restriction Enzyme (Initial Digestion)

The cDNA prepared in Reference Example described above was digested with a restriction enzyme by keeping the cDNA in any one of the following reaction solutions (A) to (C) at a specified temperature under specified conditions.

| * Composition of the reaction solution (A) (usinq Fok I) | |
|---|---|
| 10 × M buffer | 10 µl |
| 0.1% BSA (Takara Shuzo) | 10 µl |
| cDNA sample | 80 µl |
| Fok I (Takara Shuzo) (10 u/ µl) | 0.5 µl |
| Kept at 37 ° C. for 50 minutes to 1 hour. | |
| * Composition of the reaction solution (B) (usinq Bsm AI) | |
| 10 × buffer for Bsm AI (NEB) | 10 µl |
| 0.1% BSA | 10 µl |
| cDNA sample | 80 µl |
| Bsm AI (NEB) (5 u/ µl) | 1 µl |
| Kept at 55° C. for 50 minutes to 1 hour. | |
| * Composition of the reaction solution (C) (usinq Bsm FI) | |
| 10 × H buffer | 10 µl |
| Distilled water | 10 µl |
| cDNA sample | 80 µl |
| Bsm FI (NEB) (5 u/ µl) | 1 µl |
| Kept at 65 ° C. for 50 minutes to 1 hour. | |

After the completion of each of the reactions (i), (ii) and (iii) above, 3 µl of 0.25M EDTA (pH 7.5) and 2 µl of 5M NaCl were added to each reaction solution. Then, phenol extraction and ethanol precipitation were conducted and each precipitate was dissolved in 70 µl of distilled water.

(2) Addition of Adaptors

To the cDNA fragments obtained in (1) above, one of the following adaptors having the sequences described below:

C1T adaptors:

5'-B — GTACATATTGTCGTTAGAACGCT-3'  (SEQ ID NO:7)

5'-NXYZAGCGTTCTAACGACAATATGTAC-3'  (SEQ ID NO:8)

or

C1G adaptors:

5'-B — GTACATATTGTCGTTAGAACGCG-3'  (SEQ ID NO:9)

5'-NXYZCGCGTTCTAACGACAATATGTAC-3'  (SEQ ID NO:10)

(wherein B represents biotin; N represents any of the four bases; and XYZ represents one of the 64 possible sequences. When YZ=AA, AT, TA OR TT C1G adaptor were used. Otherwise, C1T adaptors were used.)

were added and kept in the following reaction solution at 16° C. overnight, to thereby ligate the cDNA fragments to the adaptors.

| * Composition of the reaction solution | |
|---|---|
| 10 × E. coli DNA ligase buffer | 1 µl |
| 100 mM (NH$_4$)$_2$ SO$_4$ | 1 µl |
| 1 pmol/ µl adaptor solution | 1 µl |
| cDNA sample digested with a class-IIS restriction enzyme | 1 µl |
| E. coli DNA ligase | 3 units |
| Distilled water to make 10 µl | |

(when the sequence XYZ did not contain G nor C, 5 pmol/µl adaptor solution and 30 units of E. coli DNA ligase were used.)

(3) Digestion with Class-IIS Restriction Enzymes (the Second Digestion)

The cDNA fragments obtained in (2) above were further digested with class-IIS restriction enzymes by keeping the cDNA sample at a specified temperature under the conditions specified below:

(i) When a Fok I digest was used:
40 µl of distilled water and 5 µl of 10× H buffer were added.
Bsm FI (1 unit) was added and kept at 65° C. for 50 minutes.
Bsm AI (1 unit) was added and kept at 55° C. for 50 minutes.

(ii) When a Bsm AI digest was used:
40 µl of distilled water and 5 µl of 10× T buffer were added.
Fok I (1 unit) was added and kept at 37° C. for 50 minutes.
Bsm FI (1 unit) was added and kept at 65° C. for 50 minutes.

(iii) When a Bsm FI digest was used:
40 µl of distilled water and 5 µl of 10× M buffer were added.
Fok I (1 unit) was added and kept at 37° C. for 50 minutes.
Bsm AI (1 unit) and 1 µl of 4M NaCl were added and kept at 55° C. for 50 minutes.

(4) Amplification by PCR (4-1) Recovery of the Adaptor Molecules with Paramagnetic Beads Immediately before use, streptavidin-coated paramagnetic beads were washed twice with 0.1% BSA and once with 1× B&W buffer (10 mM Tris-Cl pH 7.5, 1M NaCl, 1 mM EDTA) and then suspended in an equal volume of 1× B&W buffer.

To each sample, 15 μl of 5M NaCl and 5 μl of the paramagnetic beads were added, left stationary for 15 minutes and washed with 1× B&W buffer once. Then, 10 μl of 0.1M NaOH was added thereto and left stationary for 5 minutes. Thereafter, the resultant mixture was washed with 50 μl of 0.1M NaOH once, with 1× B&W buffer once and with distilled water twice.

(4-2) PCR Reaction

The reaction solutions having the compositions described below were placed in an Eppendorf tube and heated at 96° C. for 1 minute to allow a prompt initiation of reactions. Then, a thermal cycle consisting of 30 seconds at 94° C., 1 minute at 50° C. and 1 minute at 72° C. was repeated 25 to 35 times. After an extension step was carried out at 72° C. for 20 minutes, the reaction solution was cooled to room temperature.

| * Compositions of the reaction solutions (per one sample) | |
|---|---|
| (i) Enzyme reaction solution | |
| 10 × PCR buffer for Stoffel fragment | 1 μl |
| 2 mM dNTP | 1 μl |
| 25 mM MgCl$_2$ | 1.2 μl |
| Distilled water | 4.3 μl |
| 10 u/ μl Stoffel fragment *1) | 0.05 μl |
| (ii) Primer reaction solution | |
| 10 pmol/ μl fluorescent-C1T | 0.5 μl |
| 10 pmol/ μl d(T)$_{25}$ A [or d(T)$_{25}$ C, d(T)$_{25}$ G] | 2 μl |

*1) A portion of AmpliTaq DNA polymerase fragment (Perkin Elmer)

The primers are used in the combinations of JOE-C1T and d(T)$_{25}$A; FAM-C1T and d(T)$_{25}$C; and TAMRA-C1T and d(T)$_{25}$G. [JOE: 2',7'-dimethoxy-4',5'-dichloro-6-carboxyfluorescein, FAM: 5'-carboxyfluorescein, TAMRA: 6-carboxy-tetramethyl rhodamine (all manufactured by Perkin Elmer; the sequence of C1T: d(GTACATATTGTCGTTAGAACGCT)(SEQ ID NO:11)].

Alternatively, when C1G adaptors were used, the composition of the primer reaction solution is:

| 10 pmol/μl fluorescent-C1G | 0.5 μl |
|---|---|
| 10 pmol/μl d(T)$_{25}$ A [or d(T)$_{25}$ C, d(T)$_{25}$ G] | 2 μl |

The primers are used in the combinations of JOE-C1G and d(T)$_{25}$A; FAM-C1G and d(T)$_{25}$C; and TAMRA-C1G and d(T)$_{25}$G. [JOE: 2',7'-dimethoxy-4',5'-dichloro-6-carboxyfluorescein, FAM: 5'-carboxyfluorescein, TAMRA: 6-carboxy-tetramethyl rhodamine (all manufactured by Perkin Elmer; the sequence of C1G: d(GTACATATTGTCGTTAGAACGCG)(SEQ ID NO:12)].

(4-3) Preparation of Electrophoresis Samples

From each of the reaction products, a sample was taken as follows: 1 μl from the combination of FAM-C1 and d(T)$_{25}$C, 3 μl from the combination of JOE-C1 and d(T)$_{25}$A and 3 μl from the combination of TAMRA-C1 and d(T)$_{25}$G. To each sample, 5 μl of T4 DPase solution having the following composition was added and reacted at 37° C. for 40 minutes.

| Composition of T4 DPase solution (per one sample) | |
|---|---|
| 10 × M buffer | 0.5 μl |
| 2 mM dNTP | 0.5 μl |
| Distilled water | 4 μl |
| T4 DNA polymerase (Toyobo) | 1 unit |

After ethanol precipitation of the reaction solution, 3.5 μl of a buffer (80% formaldehyde, 10 mM EDTA, 6 mg/ml blue dextran) was added to the sample (i.e., precipitate), heated at 95° C. for 4 minutes, then immediately applied to the sample well of ABI 373A electrophoresis apparatus (Perkin Elmer) and run (at a constant electric power of 30W for 13 hours).

Figure 4:
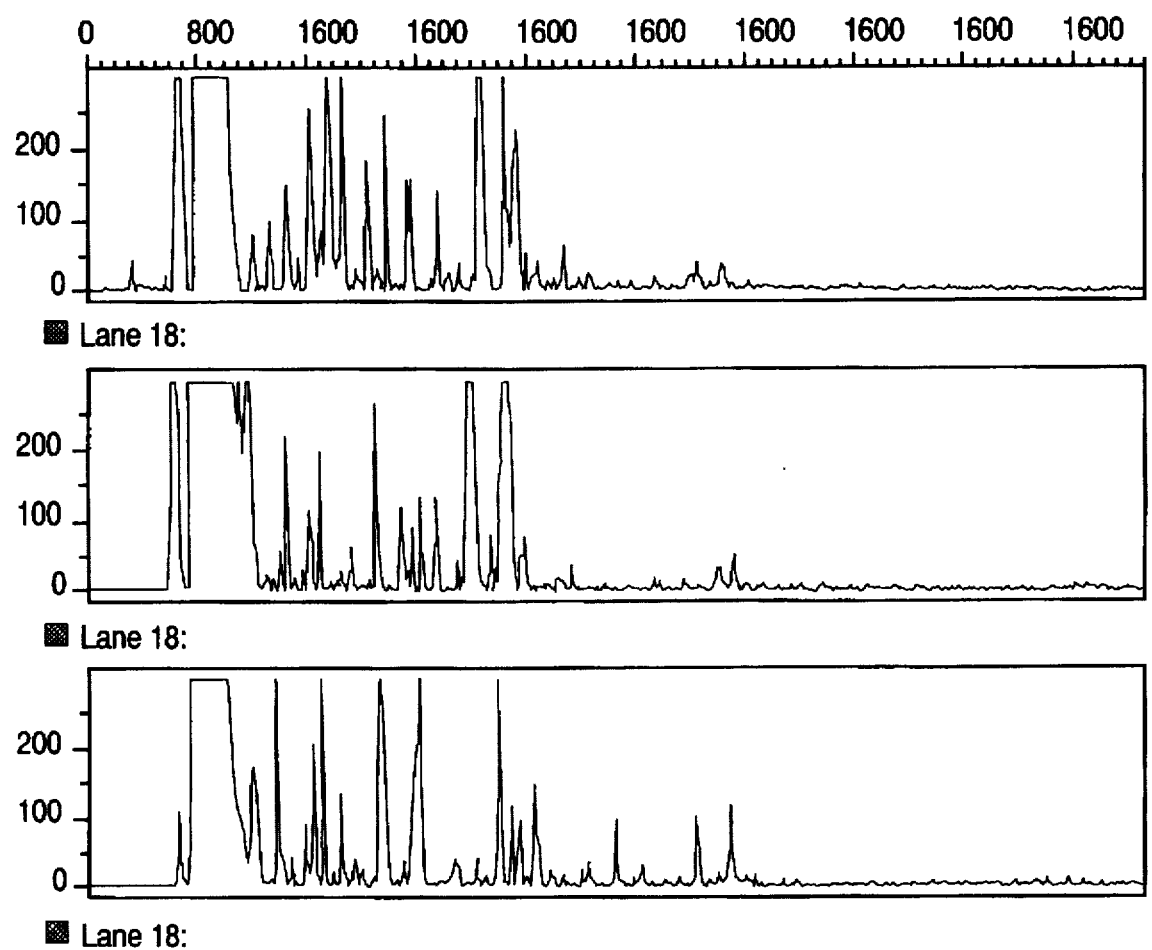
FIG. 4 shows an example of the polyacrylamide electrophoresis pattern of mouse liver RNA obtained by Method I.

FIG. 4 shows one example of the electrophoresis patterns obtained.

EXAMPLE 2

Analysis by the DNA Molecular Indexing Method (1) Digestion with a Class-II Restriction Enzyme The cDNA prepared in Reference Example described above was digested with a restriction enzyme by keeping the cDNA in the following reaction solution at a specified temperature under specified conditions.

| * Composition of the reaction solution (using EcoRI) | |
|---|---|
| 10 × high salt buffer (attached to the enzyme) | 5 μl |
| cDNA Sample | 45 μl |
| EcoRI (Toyobo or Takara Shuzo) | 5 units |
| Kept at 37° C. for 1 hour. | |

After the completion of the reaction, phenol extraction and ethanol precipitation were carried out and the total precipitate was used for the subsequent reaction.

(2) Addition of Adaptors

To the cDNA fragments obtained in (1) above, the following adaptors

5'-P—AATTCTTAACCAGGCTGAACTTGCTC-3' (SEQ ID NO:13)

5'-OH—GAGCAAGTTCAGCCTGGTTAAG-3' (SEQ ID NO:14)

were ligated by keeping the cDNA sample in the following reaction solution at 16° C. for 16 hours or more.

| * Composition of the reaction solution | |
|---|---|
| 10 × ligation buffer (similar to Toyobo's) | 2 μl |
| 2.5 pmol/ μl EcoRI adaptors | 2 μl |
| T4 DNA ligase | 150 units |
| Total volume | 20 μl |

After the completion of the reaction, phenol extraction and ethanol precipitation were carried out and the total precipitate was used for the subsequent reaction.

(3) Digestion with a Class-IIS Restriction Enzyme

The cDNA treated in (2) above was further digested with a restriction enzyme by keeping the cDNA sample in the following reaction solution at a specified temperature under specified conditions.

| * Composition of the reaction solution (using Bsm AI) | |
|---|---|
| 10 × buffer for Bsin AI(NEB) | 10 μl |
| 0.1% BSA | 10 μl |
| cDNA sample | 80 μl |
| Bsm AI (NEB) (5u/ μl) | 0.5 μl |

Kept at 65° C. for 50 minutes to 1 hour.

After the completion of the reaction, phenol extraction and ethanol precipitation were carried out and the precipitate was dissolved in 30 μl of purified water.

(4) Addition of Biotinylated Adaptors

To the cDNA fragments obtained in (3) above, the following adaptors:

C1T adaptors: 5'-B—GTACATATTGTCGTTAGAACGCT-3'
(SEQ ID NO:7)

5'-OH—NXYZAGCGTTCTAACGACAATATGTAC-3'
(SEQ ID NO:8)

C1G adaptors: 5'-B—GTACATATTGTCGTTAGAACGCG-3'
(SEQ ID NO:9)

5'-OH—NXYZCGCGTTCTAACGACAATATGTAC-3'
(SEQ ID NO:10)

(wherein B represents biotin; N represents any of the four bases; and XYZ represents one of the 64 possible sequences. When YZ=AT or TA, C1G sequences were used. Otherwise, C1T sequences were used.) were ligated by keeping the cDNA sample in the following reaction solution at 16° C. overnight.

| * Composition of the reaction solution | |
| --- | --- |
| 10 × E. coli DNA ligase buffer | 1 μl |
| 100 mM (NH$_4$)$_2$ SO$_4$ | 1 μl |
| 1 pmol/ μl adaptor solution | 1 μl |
| cDNA fragments digested with a class-IIS restriction enzyme | 1 μl |
| E. coli DNA ligase | 3 units |
| Distilled water | to make 10 μl |

(when the sequence XYZ did not contain G nor C, 5 pmol/μl adaptor solution and 6 units of E. coli DNA ligase were used.)

(5) Amplification by PCR (5-1) Recovery of the Adaptor Molecules with Paramagnetic Beads Immediately before use, streptavidin-coated paramagnetic beads were washed twice with 0.1% BSA and once with 1× B&W buffer (10 mM Tris-Cl pH 7.5, 1M NaCl, 1 mM EDTA) and then suspended in an equal volume of 1× B&W buffer.

To the sample, 15 μl of 5M NaCl and 5 μl of the paramagnetic beads were added, left stationary for 15 minutes and washed with 1× B&W buffer once. Then, 10 μl of 0.1M NaOH was added thereto and left stationary for 5 minutes. Thereafter, the resultant mixture was washed with 50 μl of 0.1M NaOH once, with 1× B&W buffer once and with distilled water twice.

(5-2) PCR Reaction

The reaction solutions having the compositions described below were placed in an Eppendorf tube and heated at 96° C. for 1 minute to allow a prompt initiation of reactions. Then, a thermal cycle consisting of 30 seconds at 94° C., 1 minute at 50° C. and 1 minute at 72° C. was repeated 25 to 35 times. After an extension step was carried out at 72° C. for 20 minutes, the reaction solution was cooled to room temperature.

| * Compositions of the reaction solutions (per one sample) | |
| --- | --- |
| (i) Enzyme reaction solution | |
| 10 × PCR buffer for Stoffel fragment | 1 μl |
| 2 mM dNTP | 1 μl |
| 25 mM MgCl$_2$ | 1.2 μl |
| Distilled water | 4.3 μl |
| 10 u/ μl Stoffel fragment *1) | 0.05 μl |
| (ii) Primer reaction solution | |
| 10 pmol/ μl fluorescent-C1S primer | 0.5 μl |
| 10 pmol/ μl λ gt10 forward primer | 0.5 μl |

*1) A portion of AmpliTaq DNA polymerase fragment (Perkin Elmer)

The two kinds of primers having the following sequences are used in combination:

5'-OH—GTACATATTGTCGTTAGAACGC-3'(C1S primer)
(SEQ ID NO:15)

5'-OH—GAGCAAGTTCAGCCTGGTTAAG-3'(λ gt10 forward primer)
(SEQ ID NO: 14)

(5-3) Preparation of Electrophoresis Samples

A 3 μl sample was taken from the reaction products and 5 μl of T4 DPase solution having the following composition was added thereto. The resultant mixture was reacted at 37° C. for 40 minutes.

| * Composition of T4 DPase solution (per one sample) | |
| --- | --- |
| 10 × M buffer | 0.5 μl |
| 2 mM dNTP | 0.5 μl |
| Distilled water | 4 μl |
| T4 DNA polymerase (Toyobo) | 1 unit |

After ethanol precipitation of the reaction solution, 3.5 μl of a buffer (80% formaldehyde, 10 mM EDTA, 6 mg/ml blue dextran) was added to the sample (i.e., precipitate), heated at 95° C. for 4 minutes, then immediately applied to the sample well of ABI 373A electrophoresis apparatus (Perkin Elmer) and run (at a constant electric power of 30W for 13 hours).

Figure 5:
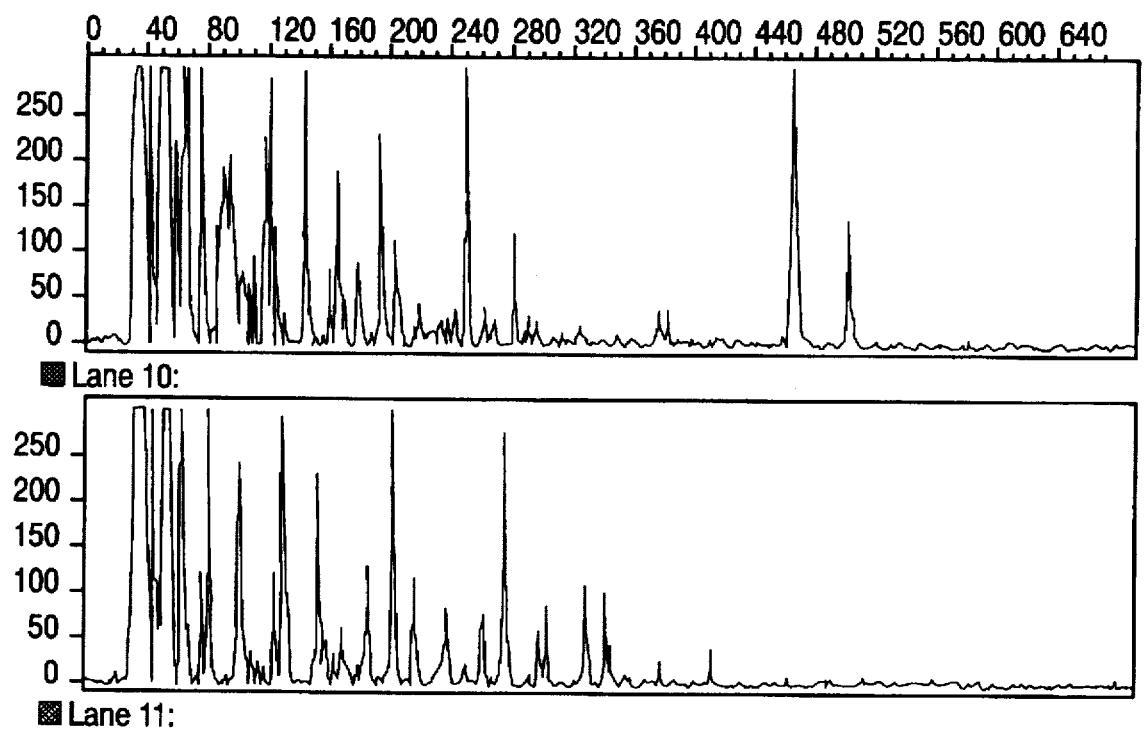
FIG. 5 shows an example of the polyacrylamide electrophoresis pattern of an amplified product from mouse liver RNA obtained by Method II.

FIG. 5 shows one example of the electrophoresis patterns obtained.

---

What is claimed is:

1. A method for determining the molecular index of a cDNA preparation comprising the following steps:

(a) digesting the cDNA preparation which has been reverse-transcribed by oligo-dT priming from a RNA preparation with a first class-IIS restriction enzyme;

(b) ligating each of the resultant cDNA fragments to an adaptor from a pool of 64 adapters cohesive to all possible overhangs of DNA fragments produced by the digestion in step (a) and thereby producing a ligation product, wherein each adaptor from said pool of adaptors has an overhang sequence and comprises a biotinylated oligonucleotide strand and a non-biotinylated oligonucleotide strand which has the overhang sequence;

(c) digesting the resultant ligation product with a second and a third class-IIS restriction enzymes which are different from the first class-IIS restriction enzyme used in step (a) and thereby obtaining a cDNA sample;

(d) recovering cDNA fragments which are ligated to adaptors from the cDNA samples by binding to streptavidin, removing non-biotinylated strands of polynucleotides from the recovered cDNA fragments, and thereby obtaining a single-stranded cDNA sample;

(e) amplifying the single-stranded cDNA sample by polymerase chain reaction using a first primer comprising a sequence identical to a segment or the whole of the biotinylated oligonucleotide strand of the adaptor and a second primer which is an anchor oligo-dT primer selected from the group consisting of $d(T)_{25}A$, $d(T)_{25}C$ and $d(T)_{25}G$, and thereby obtaining an amplification product; and (f) separating the amplification product by denaturing polyacrylamide gel electrophoresis, recording the molecular sizes of DNA molecules in the amplification product, and thereby obtaining the molecular index of the cDNA preparation.

2. A method for determining the molecular index of a cDNA preparation comprising the following steps:

(a) digesting the cDNA preparation which has been reverse-transcribed by oligo-dT priming from a RNA preparation with a first class-IIS restriction enzyme;

(b) ligating each of the resultant cDNA fragments to an adaptor from a pool of 64 adapters cohesive to all possible overhangs of DNA fragments produced by the digestion in step (a) and thereby producing a ligation product, wherein each adaptor from said pool of adaptors has an overhang sequence and comprises a biotinylated oligonucleotide strand and a non-biotinylated oligonucleotide strand which has the overhang sequence;

(c) digesting the resultant ligation product with a second and a third class-IIS restriction enzymes which are different from the first class-IIS restriction enzyme used in step (a) and thereby obtaining a first cDNA sample;

(d) obtaining a second cDNA sample by repeating steps (a) to (c), wherein in step (a), the cDNA preparation is digested by the second class-IIS restriction enzyme, and in step (c), the ligation product is digested with the first and third class-IIS restriction enzymes;

(e) obtaining a third cDNA sample by repeating steps (a) to (c), wherein in step (a), the cDNA preparation is digested by the third class-IIS restriction enzyme, and in step (c), the ligation product is digested with the first and second class-IIS restriction enzymes;

(f) recovering cDNA fragments which are ligated to adaptors from the first, second and third cDNA samples by binding to streptavidin, removing non-biotinylated strands of polynucleotides from the recovered cDNA fragments, and thereby obtaining a single-stranded cDNA sample;

(g) amplifying the single-stranded cDNA sample by polymerase chain reaction using a first primer comprising a sequence identical to a segment or the whole of the biotinylated oligonucleotide strand of the adaptor and a second primer which is an anchor oligo-dT primer selected from the group consisting of $d(T)_{25}A$, $d(T)_{25}C$ and $d(T)_{25}G$, and thereby obtaining an amplification product; and (h) separating the amplification product by denaturing polyacrylamide gel electrophoresis, recording the molecular sizes of DNA molecules in the amplification product, and thereby obtaining the molecular index of the cDNA preparation.

3. The method according to claim 1 or 2, wherein the class-IIS restriction enzymes are used in a combination of Fok I, Bsm AI and Bsm FI.

4. The method according to claim 1 or 2, wherein the cDNA preparation has been synthesized by reverse-transcribing RNA using as primer a mixture of the following oligonucleotides:

5' OH—GGATCCT$_{16}$A-3'  (SEQ ID NO:4),

5' OH—CAGCTGT$_{16}$C-3'  (SEQ ID NO:5), and

5' OH—CTCGAGT$_{16}$G-3'  (SEQ ID NO:6).

5. The method according to claim 4, wherein the amplification of the single-stranded cDNA sample is carried out using as the second primer an oligonucleotide selected from the group consisting of:

5' OH—GGATCCT$_{16}$A-3'  (SEQ ID NO:4),

5' OH—CAGCTGT$_{16}$C-3'  (SEQ ID NO:5), and

5' OH—CTCGAGT$_{16}$G-3'  (SEQ ID NO:6), instead of an anchored oligo-dT primer.

6. The method according to claim 1 or 2, wherein the first or second primer is labeled with a marker.

7. The method according to claim 5, wherein the marker is an radioactive atom, fluorescent dye or enzyme.

8. The method according to claim 1 or 2, wherein the streptavidin is attached to paramagnetic beads.

9. The method according to claim 1 or 2, wherein the RNA preparation is isolated from an animal cell or tissue, or a plant cell or tissue.

10. A method for determining the molecular index of a cDNA or DNA preparation comprising the following steps:

(a) digesting the cDNA or DNA preparation with a class-II restriction enzyme and thereby producing a first cDNA fragment preparation or first DNA fragment preparation, wherein the cDNA preparation has been reverse-transcribed by oligo-dT priming from a RNA preparation;

(b) ligating each cDNA fragment in the first cDNA preparation or each DNA fragment in the first DNA fragment preparation to a first adaptor which is cohesive to the overhang of cDNA fragments or DNA fragments produced by the class-II restriction enzyme and thereby producing a first ligated cDNA preparation or first ligated DNA preparation;

(c) digesting the first ligated cDNA preparation or first ligated DNA preparation with a class-IIS restriction enzyme and thereby producing a second cDNA fragment preparation or second DNA fragment preparation;

(d) ligating each cDNA fragment in the second cDNA fragment preparation or each DNA fragment in the second DNA fragment preparation to a second adaptor from a pool of 64 adapters cohesive to all possible overhangs of cDNA fragments or DNA fragments produced by the digestion with the class-IIS restriction enzyme and thereby producing a second ligated cDNA preparation or second ligated DNA preparation, wherein each second adaptor from said pool of adaptors has an overhang sequence and comprises a biotinylated oligonucleotide strand and a non-biotinylated oligonucleotide strand which has the overhang sequence;

(e) recovering cDNA fragments or DNA fragments which are ligated to adaptors from the second ligated cDNA preparation or second ligated DNA preparation by binding to streptavidin, removing non-biotinylated strands of polynucleotides from the recovered cDNA fragments or DNA fragments, and thereby obtaining a single-stranded cDNA or DNA sample;

(f) amplifying the single-stranded cDNA or DNA sample by polymerase chain reaction using a first primer comprising a sequence identical to a segment or the whole of the biotinylated oligonucleotide strand of the second adaptor and a second primer comprising a sequence identical or complementary to a segment or the whole of an oligonucleotide strand of the first adaptor, and thereby producing an amplification product; and (g) separating the amplification product by denaturing polyacrylamide gel electrophoresis, recording the molecular sizes of amplified cDNA or DNA molecules in the amplification product, and thereby obtaining the molecular index of the cDNA or DNA preparation.

11. The method according to claim 10, wherein the class-IIS restriction enzyme is Fok I, Bsm AI, Bsm FI, Sfa NI or Bbv I.

12. The method according to claim 10, wherein the first or second primer is labeled with a marker.

13. The method according to claim 12, wherein the marker is an radioactive atom, fluorescent dye or enzyme.

14. The method according to claim 10, wherein the streptavidin is attached to paramagnetic beads.

15. The method according to claim 10, wherein the DNA preparation or RNA preparation is isolated from an animal cell or tissue, or a plant cell or tissue.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 26 base pairs
( B ) TYPE: nucleic acid
( C ) STRANDEDNESS: unknown
( D ) TOPOLOGY: unknown (  i  i  ) MOLECULE TYPE: other nucleic acid (  x  i  ) SEQUENCE DESCRIPTION: SEQ ID NO:1:

TTTTTTTTT TTTTTTTTT TTTTA  26

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:2:

TTTTTTTTT TTTTTTTTT TTTTC  26

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:3:

TTTTTTTTT TTTTTTTTT TTTTG  26

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:4:

GGATCCTTTT TTTTTTTTT TTA  23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:5:

CAGCTGTTTT TTTTTTTTT TTC  23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:6:

```
CTCGAGTTTT TTTTTTTTT TTG                                                                    23
```

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:7:

```
GTACATATTG TCGTTAGAAC GCT                                                                   23
```

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:8:

```
NNNNAGCGTT CTAACGACAA TATGTAC                                                               27
```

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:9:

```
GTACATATTG TCGTTAGAAC GCG                                                                   23
```

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:10:

```
NNNNCGCGTT CTAACGACAA TATGTAC                                                               27
```

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:11:

```
GTACATATTG TCGTTAGAAC GCT                                                                   23
```

( 2 ) INFORMATION FOR SEQ ID NO:12:

( i ) SEQUENCE CHARACTERISTICS:
  ( A ) LENGTH: 23 base pairs
  ( B ) TYPE: nucleic acid
  ( C ) STRANDEDNESS: unknown
  ( D ) TOPOLOGY: unknown ( i i ) MOLECULE TYPE: other nucleic acid ( x i ) SEQUENCE DESCRIPTION: SEQ ID NO:12:

GTACATATTG TCGTTAGAAC GCG                                    23

( 2 ) INFORMATION FOR SEQ ID NO:13:

( i ) SEQUENCE CHARACTERISTICS:
    ( A ) LENGTH: 26 base pairs
    ( B ) TYPE: nucleic acid
    ( C ) STRANDEDNESS: unknown
    ( D ) TOPOLOGY: unknown ( i i ) MOLECULE TYPE: other nucleic acid ( x i ) SEQUENCE DESCRIPTION: SEQ ID NO:13:

AATTCTTAAC CAGGCTGAAC TTGCTC                                 26

( 2 ) INFORMATION FOR SEQ ID NO:14:

( i ) SEQUENCE CHARACTERISTICS:
    ( A ) LENGTH: 22 base pairs
    ( B ) TYPE: nucleic acid
    ( C ) STRANDEDNESS: unknown
    ( D ) TOPOLOGY: unknown ( i i ) MOLECULE TYPE: other nucleic acid ( x i ) SEQUENCE DESCRIPTION: SEQ ID NO:14:

GAGCAAGTTC AGCCTGGTTA AG                                     22

( 2 ) INFORMATION FOR SEQ ID NO:15:

( i ) SEQUENCE CHARACTERISTICS:
    ( A ) LENGTH: 22 base pairs
    ( B ) TYPE: nucleic acid
    ( C ) STRANDEDNESS: unknown
    ( D ) TOPOLOGY: unknown ( i i ) MOLECULE TYPE: other nucleic acid ( x i ) SEQUENCE DESCRIPTION: SEQ ID NO:15:

GTACATATTG TCGTTAGAAC GC                                     22

( 2 ) INFORMATION FOR SEQ ID NO:16:

( i ) SEQUENCE CHARACTERISTICS:
    ( A ) LENGTH: 18 base pairs
    ( B ) TYPE: nucleic acid
    ( C ) STRANDEDNESS: unknown
    ( D ) TOPOLOGY: unknown ( i i ) MOLECULE TYPE: other nucleic acid ( x i ) SEQUENCE DESCRIPTION: SEQ ID NO:16:

TTTTTTTTTT TTTTTTTT                                          18